United States Patent
Breuer et al.

(10) Patent No.: US 8,532,255 B2
(45) Date of Patent: Sep. 10, 2013

(54) PREPARATION AND PRESENTATION OF PATIENT-INDIVIDUAL PANORAMIC VISUALIZATIONS

(75) Inventors: Manfred Breuer, Alfter (DE); Nils Hanßen, Bonn (DE); Joachim Hey, Bornheim (DE)

(73) Assignee: Sicat GmbH & Co. KG, Bonn (DE)

( * ) Notice: Subject to any disclaimer, the term of this patent is extended or adjusted under 35 U.S.C. 154(b) by 359 days.

(21) Appl. No.: 12/990,525

(22) PCT Filed: Mar. 5, 2009

(86) PCT No.: PCT/EP2009/052642
§ 371 (c)(1),
(2), (4) Date: Jan. 24, 2011

(87) PCT Pub. No.: WO2009/132880
PCT Pub. Date: Nov. 5, 2009

(65) Prior Publication Data
US 2011/0109630 A1    May 12, 2011

(30) Foreign Application Priority Data

May 2, 2008   (DE) .......................... 10 2008 021 926

(51) Int. Cl.
*A61B 6/14*      (2006.01)
(52) U.S. Cl.
USPC ........................................................ 378/38

(58) Field of Classification Search
USPC .................................. 378/4, 38–40; 345/424
See application file for complete search history.

(56) References Cited

U.S. PATENT DOCUMENTS

| | | | |
|---|---|---|---|
| 6,493,415 B1 | 12/2002 | Arai et al. | |
| 7,787,586 B2 | 8/2010 | Yoshimura et al. | |
| 2006/0275740 A1 | 12/2006 | Singh et al. | |
| 2008/0232540 A1 | 9/2008 | Yoshimura et al. | |

FOREIGN PATENT DOCUMENTS

| | | |
|---|---|---|
| DE | 100 84 386 T1 | 2/2002 |
| DE | 10 2005 0558986 | 5/2007 |
| DE | 10 2008 010 537 A1 | 8/2008 |

OTHER PUBLICATIONS

International Search Report, Date of Completion Jul. 8, 2009, Date of mailing Jul. 17, 2009, 3 pages.
"Synthesizing panoramic radiographs by unwrapping dental CT data", Tohank S et al., Engineering in Medicine and Biology Society, 2006. EMBS 06, 26th Annual International Conference of the IEEE, IEEE, Piscataway, NJ, USA, Aug. 30, 2006, pp. 3329-3332, XP031390350 ISBN:978-1-4244-0032-4, figures 3,4, table 2.1.

*Primary Examiner* — Jurie Yun
(74) *Attorney, Agent, or Firm* — Millen, White, Zelano & Branigan, P.C.

(57) ABSTRACT

The invention relates to a method for generating and presenting a panorama image of a jaw region, where first a set of volume data representing the jaw region of a patient is generated by means of a tomographic method.

12 Claims, 2 Drawing Sheets

PREPARATION AND PRESENTATION OF PATIENT-INDIVIDUAL PANORAMIC VISUALIZATIONS

This invention relates to a method for preparation and presentation of a panoramic visualization of a maxillary region, first of all a set of volume data that represent the maxillary region of a patient being generated by means of a tomographic method, the volume data being composed of a plurality of individual volume elements ("voxels").

These two-dimensional panoramic visualizations of rows of teeth and maxillary arches have been known and popular for a long time in dentistry and oral surgery since they provide the attending physician a good overview of the situation. Especially meaningful pictures are taken along curved projection planes that run matched to that of the maxillary bone. These panoramic pictures (orthopantomograms) can be prepared as "classic" X-ray images with systems in which an x-ray tube and a detector are moved around the head of the patient.

Since the introduction of tomographic imaging methods, these panoramic visualizations are also computed from volume data. In doing so, the pictures computed in this way are presented such that they are similar to the customary pictures prepared using x-ray images. These methods thus produce more or less "simulated" orthopantomogram images from three-dimensional video data so that dentists can prepare their diagnoses using familiar views. Tn this procedure, a plurality of possibilities for optimization of the pictures that offer high-resolution data sets can be used. In this way, panoramic visualizations with high informational value are produced.

Fundamentally, in this visualization of three-dimensional video data, a projection of the data along projection beams is carried out, and the result is displayed as a two-dimensional picture on a display device. In this projection, physical properties such as emissions or attenuations can be considered that are assigned to the individual three-dimensional elements of the video data (voxels) using transfer functions. Since this visualization is ultimately based on a projection of density values, it is necessarily similar to the aforementioned conventional radioscopy.

This method for preparation of panoramic images from tomographic data is known, for example, from US 200610275740 A1. In order to be able to follow the anatomical structures in the computation of the preferred direction, a development surface that is curved in space is determined on which the projection beams are vertical. In this way, a "development" of data with a certain thickness is achieved. To determine the development surface, the method first proceeds from an initializing cutting plane that is horizontally aligned with respect to a seated individual. In this cutting plane, a line that represents the contour within the maxillary arch is defined that forms the base of a projection plane that is to be prepared. The projections necessary for the panoramic visualization are carried out starting from this development surface. The method that is disclosed in US 2006/0275740 A1, however, only to a minor degree matches the actual anatomical conditions that can vary greatly in the vertical.

The object of the invention is now to devise a generic method that can be easily implemented and that generates a panoramic visualization that is meaningful to the attending physician and that is easily adapted to the actual anatomical conditions.

One important fundamental idea of the invention is first of all to establish not only one, but several horizontal cutting planes that intersect the jaw. In each of these cutting planes then, a contour surface of the jaw that is bordered by one inner and one outer contour line can be defined. This determination of the contour surface can take place automatically using the voxel values that change suddenly on the solid jaw. Within each contour surface, for example, an anatomy curve is defined, for example, based on weighting algorithms. It is especially critical to the invention at this point to determine a common development curve from these "layer-individual" anatomy curves of cutting planes that lie on top of one another, and this "determination" can take place by weighted computation averaging in the proper sense. This development curve then defines a development surface that is especially vertical in space.

Then, based on the development surface and for each cutting plane in turn, projection beams are defined that are vertical on the development surface and that intersect the respective contour line that lies in the cutting plane. The orthopantomogram is prepared at this point by integration intervals that are located especially within the contour line being defined over fragments of the projection beams. Then, the information of the respective voxel is integrated over this integration interval. The orthopantomogram then consists of the plurality of the integrals that have been determined in this way.

The special advantage of this procedure is that for a set of cutting planes, a common "best" development surface can be computed that is optimally matched to the individual anatomical conditions of the respective patient. The development surface more or less tangentially conforms optimally to the row of teeth that runs individually for each patient for certain cutting planes at the same time. In this way, for example, it can be ensured that adjacent teeth of differently shaped upper and lower jaws are not superimposed in the projection picture. Another advantage is that in the manner according to the invention, which can correspond to averaging, a development surface that is as arched as little as possible is formed with which three-dimensional distortions of high curvature can be avoided in the projection picture. The danger that intersections of the projection beams will occur due to the overly curved regions of the development surfaces, as is possible in the prior art, can be diminished in this way. Especially high contrast in the anatomical structures to be visualized can be achieved by the process according to the invention due to the focal curves that are different for different layers and that are matched individually to the patient.

With the procedure according to the invention, the midpoints of the individual projection beam segments are no longer determined by the projection plane itself. Instead, they are computed through the section of each (actually infinitely long) beam with a curved focal plane that is optimally matched to the anatomy that is to be visualized.

In one especially advantageous embodiment, the contribution of each voxel to the projection value is determined by the sequence of voxel values along the projection direction so that the voxels remote from the focal curve are semi-transparently hidden by .the voxels nearer the focal curve. This results in additional exponential weighting of the voxels nearer the focal curve; this leads to increased contrast within these voxel regions. Moreover, in contrast to a pure x-ray projection, the three-dimensional location of individual structures can be assessed in depth to one another by the semi-transparent concealment.

Due to the "spongy" structure of the jaw bone, which structure is provided with many holes, detection of the external bone edges (contour lines) can only be done with difficulty with a local operator; ultimately, many of the inner edges that belong to the holes would not be distinguishable from the outer bone edges due to the limited "horizon" of the local operator. By preprocessing with a morphological closing operator on the gray-scale value data, holes in the bones that do not exceed a minimum size can be closed. By a suitable choice of the minimum size, only edges that (relating to the size of the structure) are dominant edges are detected. In this respect, it is advantageous to determine each focal curve by preprocessing by means of morphological operators or by a combination of edges and intensity information.

It is also advantageous to determine the contribution of each voxel on the projection value by the voxel values in the vicinity of the voxel. Here, the size of the vicinity can be variable and can also comprise the entire volume especially for each voxel. In this way, the contrast of structures of a certain shape (structurally) or of a certain frequency (statistically) within the vicinity can be emphasized in a controlled manner. Thus, for example, nerve channels that have a typical diameter can be made visible especially easily (structurally). Furthermore, the contrast can be diminished by especially frequently occurring voxel values that with great probability contain little diagnostic information since they belong, for example, to soft tissue.

The invention is described in more detail below using FIGS. 1 and 2. Here:

Figure 1:
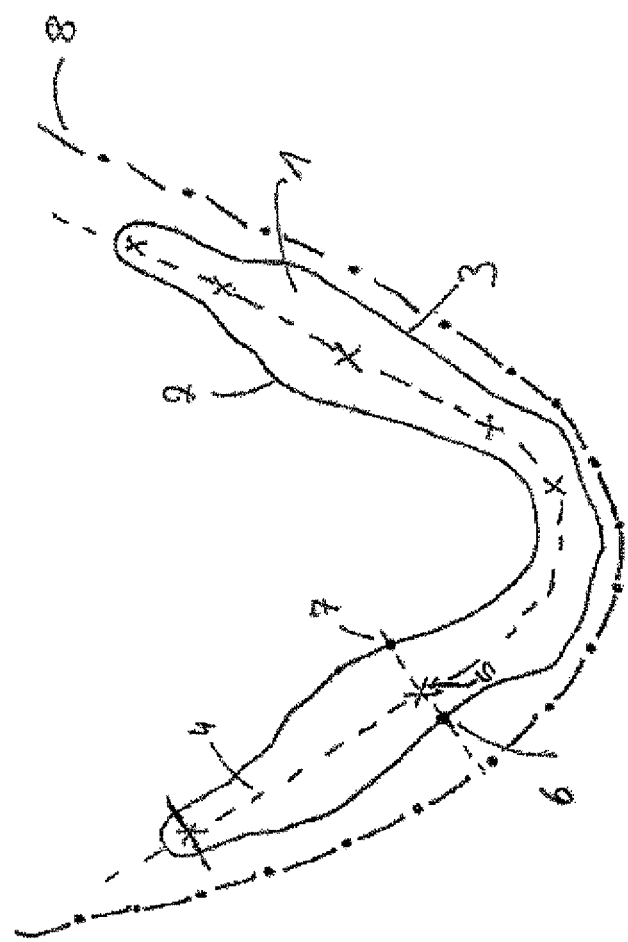
FIG. 1 shows the generation of focal curves.

Steps of the method according to the invention are shown using FIG. 1. Here, a set of volume data that represent the maxillary region of a patient was generated first by means of a tomographic method. These volume data are composed of a plurality of individual volume elements ("voxels"). Within the volume data, individual cutting planes are extracted that run horizontally through the jaw. FIG. 1 shows one of these cutting planes, each of the cutting planes being at least one voxel strong. Optionally, however, it is possible to average over a few "voxel" layers. In the cutting plane, the contour surface 1 of the cut jawbone can be recognized; it is bordered by an inner contour line 2 and an outer contour line 3. The contour lines 2 and 3 can be automatically determined by means of corresponding recognition software within the cutting planes, since the density values represented by the voxels change drastically at these sites.

As the next step, within each contour surface 1, a focal curve 4 is defined that arises as a connection of individual focal points 5. To find the focal points 5, points 6 at a certain distance from one another can be defined on one of the two contour lines, here the outer contour line 3, for each of the points 6 the opposite point 7 as near as possible in this case being found on the other contour line, in this case the inner contour line 2. The midpoint of the distance that links the two points 6 and 7 can be defined as a focal point 5, and averaging of the adjacent points can also take place at this site. The focal curve 4 is placed as a center line through all focal points 5. The individual focal curves thus come to rest as center lines in the middle in the bone and/or in the rows of teeth. The process is the same for all cutting planes, so that a set of focal curves 4 of varied camber that lie on top of one another arises. FIG. 1 shows another focal curve from another cutting plane as a dot-dash curve 8.

In cases in which teeth are missing on one side of the jaw, the shape of the focal curves can be taken over in segments from the side that is the other one at the time. This interpolation can take place automatically, since missing teeth or missing bones can be automatically recognized.

Figure 2:
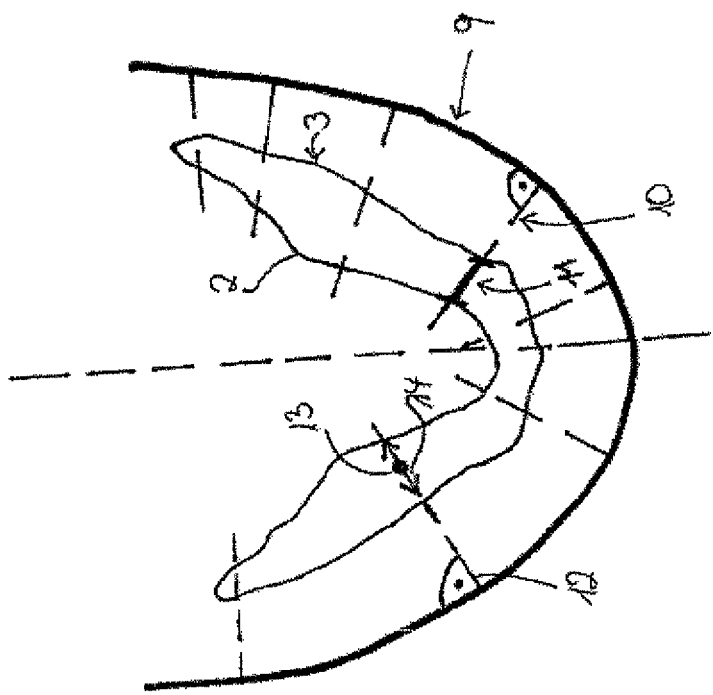
FIG. 2 shows the generation of integration intervals.

In the next step, a common development curve is determined from all focal curves of the cutting planes that lie on top of one another, and this "determination" in the simplest case can be mathematical averaging that is optionally weighted. In this case, the development curve 9 is determined that—also for reasons of clarity—runs in turn in front of the contour surface 1 (see FIG. 2). In this case, an offset had to be added to the geometrical averaging of the focal curves. A development surface that is not shown, that is set up vertically in this case, and that is thus arranged more or less as an elliptically curved wall in front of the jaw, is defined by this development curve 9. In this example, the development curve 9 is symmetrical to the axis 15, so that in the panoramic visualization, comparisons can be drawn between the left half and the right half of the jaw.

In an additional method, starting from the development surface (here shown by the development curve 9), each cutting plane is used in turn, projection beams 10 being defined that are vertical on the development surface in the cutting plane and that intersect the respective contour lines 2 and 3. On each of the projection beams 10, at this point integration intervals 11 are defined that in this case extend from the inner contour line 2 to the outer contour line 3. By way of these integration intervals 11, the voxel information is integrated, the result of each such integration yielding one pixel of the panoramic visualization at a time. In this case, the contribution of each voxel to the projection value is automatically determined using the voxel data by a computer program.

In one special embodiment using the underlying anatomy of the jaw, on each projection beam 12, a reference point 13 is defined from which a projection is determined by integrations especially to either side (arrows 14) along the projection direction. In this way, the contrast can be optimized since only one segment of the projection beam contributes to the evaluation due to the minimized length of the projection beams. Furthermore, in contrast to the prior art, the projection direction is passed through bilaterally in both directions of the arrows 14 starting from the reference point 13 by this procedure. For this reason, the site with the highest contrast on each projection beams always lies on the focal plane.

The invention claimed is:

1. A method for preparing and presenting a panoramic visualization of a maxillary region, wherein a set of volume data representing the maxillary region of a patient is generated by a tomographic method, wherein the volume data comprises a plurality of individual volume elements, said method comprising establishing several horizontal cutting planes that intersect a jaw, and defining, within each cutting plane, a contour surface (1) of the jaw that is bordered by an inner contour line (2) and an outer contour line (3), defining focal curves (4, 8) within the contour surfaces (1), determining a common development curve (9) from the focal curves (4, 8) of the cutting planes that lie on top of one another, wherein the development curve (9) defines a development surface that has been set up optionally vertically, defining, starting from the development surface in each cutting plane, projection beams (10, 12) that are perpendicular on the development surface and intersect the respective contour lines (2, 3), defining, on the projection beams (10,12), integration intervals (11) on which information of the volume elements is integrated, and integrating to form one pixel of the panoramic visualization at a time.

2. A method according to claim 1, wherein one reference point (13) is defined by an underlying anatomy on each projection beam (10, 12), from which a projection is determined by integration optionally to either side, along the projection direction.

3. A method according to claim 2, wherein each reference point (13) is formed from the intersection point of the projection beam and the focal curve (4, 8) that is determined for the respective cutting plane.

4. A method of claim 2 wherein the projection is determined by integration to either side, along the projection direction.

5. A method according to claim 1, wherein the integration intervals are defined within the contour surfaces (1) and extend optionally from the inner contour line (2) to the outer contour line (3).

6. A method of claim 5 wherein the integration intervals are defined within the contour surfaces (1) and extend from the inner contour line (2) to the outer contour line (3).

7. A method according to claim 1, wherein the focal curves (4, 8) and/or the development curve (9) are automatically determined by a computer program using voxel data that represent an underlying anatomy.

8. A method according to claim 1, wherein the focal curves (4, 8) are each defined as center lines within the contour surfaces (1) and thus come to rest in the middle in a bone or in one or more rows of teeth.

9. A method according to claim 8, wherein each focal curve (4, 8) is determined by preprocessing by morphological operators or by a combination of edges and intensity information by an underlying anatomy.

10. A method according to claim 1, wherein each focal curve (4, 8) and thus also the development curve (9) is mirror-symmetrical with respect to the midpoint of its arc length.

11. A method according to claim 10, wherein based on anatomical conditions, missing parts of focal curves (4, 8) are replaced by the corresponding parts of the opposite side in order to extrapolate or interpolate missing teeth and/or missing bones.

12. A method of claim 1 wherein the development surface has been set up vertically.

* * * * *

UNITED STATES PATENT AND TRADEMARK OFFICE
CERTIFICATE OF CORRECTION

PATENT NO.       : 8,532,255 B2                    Page 1 of 1
APPLICATION NO. : 12/990525
DATED            : September 10, 2013
INVENTOR(S)      : Breuer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 441 days.

Signed and Sealed this

Fifteenth Day of September, 2015

Michelle K. Lee
*Director of the United States Patent and Trademark Office*